United States Patent
Poorman-Ketchum

[19]

[11] Patent Number: 6,149,600
[45] Date of Patent: Nov. 21, 2000

[54] BLOOD PRESSURE MEASURING DEVICE

[76] Inventor: Rebekah Poorman-Ketchum, R.R.#6, Box 395, Auburn, N.Y. 13021

[21] Appl. No.: 09/074,850

[22] Filed: May 8, 1998

[51] Int. Cl.⁷ ..................................................... A61B 5/02
[52] U.S. Cl. ........................... 600/499; 600/490; 606/202
[58] Field of Search .................... 600/499, 490, 600/491; 602/62, 20, 63, 53, 75; 606/202

[56] References Cited

U.S. PATENT DOCUMENTS

| | | | |
|---|---|---|---|
| 3,699,945 | 10/1972 | Hanafin | 600/499 |
| 3,765,405 | 10/1973 | Natkanski | 600/499 |
| 4,572,205 | 2/1986 | Sjonell | 600/499 |
| 4,716,906 | 1/1988 | Ruff | 600/499 |
| 4,901,732 | 2/1990 | Williams | 600/499 |
| 5,243,991 | 9/1993 | Marks | 600/499 |
| 5,584,853 | 12/1996 | McEwen | 600/499 |
| 5,626,142 | 5/1997 | Marks | 600/499 |
| 5,660,182 | 8/1997 | Kuroshaki et al. | 600/499 |
| 5,746,213 | 5/1998 | Marks | 600/499 |
| 5,792,091 | 8/1998 | Staudinger | 602/62 |

*Primary Examiner*—Max Hindenburg
*Assistant Examiner*—Navin Natnithithadha
*Attorney, Agent, or Firm*—Wall Marjama Bilinski & Burr

[57] ABSTRACT

In the pressure cuff of the present invention, an end portion of a cuff comprises a pair of separable first and second tail sections, each having a coupling mechanism, such as sections of hook and loop type fastening material formed thereon. A complementary coupling mechanism is formed on the bladder section. When the cuff is wrapped about an arm having a nonuniform circumference, then the tail sections can be coupled at different lengths to the bladder section of the cuff, so that the bladder section, when inflated, supplies relatively even pressure across a substantial length of the brachial artery.

7 Claims, 4 Drawing Sheets

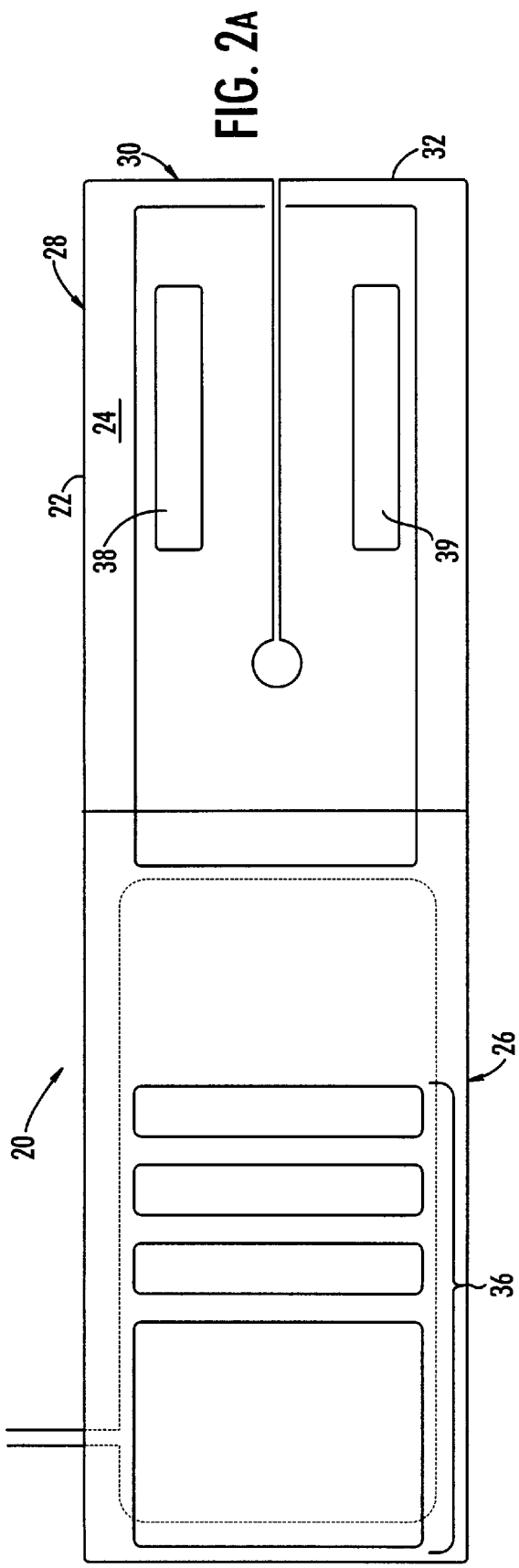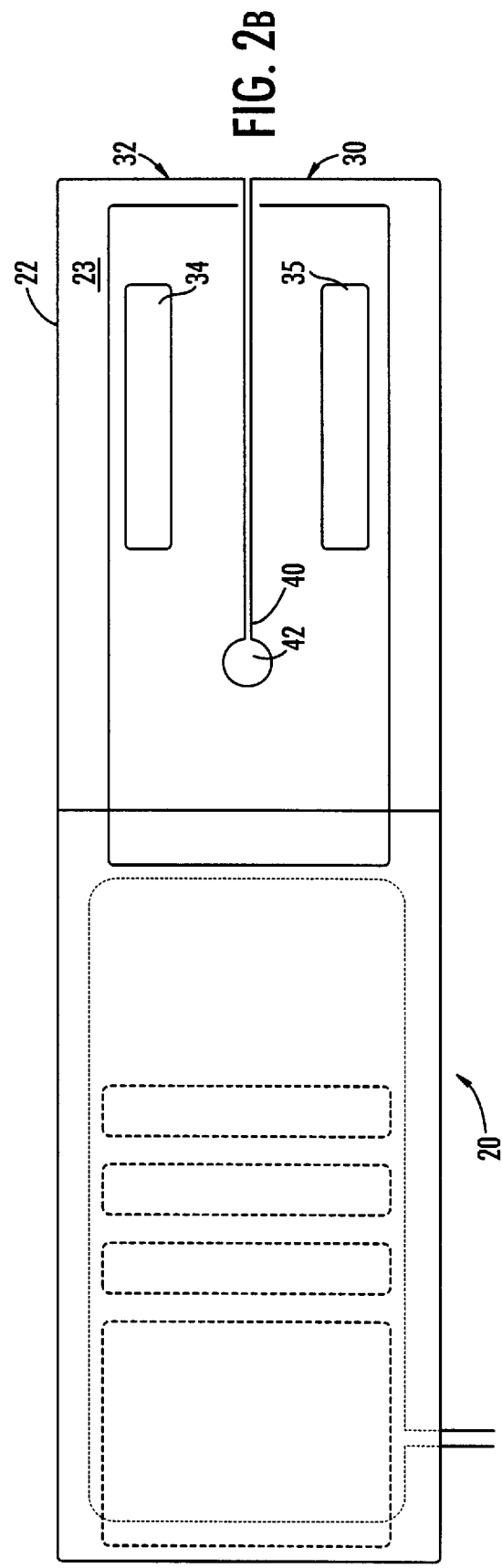

BLOOD PRESSURE MEASURING DEVICE

BACKGROUND OF THE INVENTION

1. Field of the Invention

The invention relates generally to blood pressure measuring devices and particularly to a new cuff design for a blood pressure measuring device.

2. Background of the Prior Art

According to the auscultatory method of measuring blood pressure, a health care provider wraps a pneumatic cuff, including an inflatable section and an end section, around an arm of a patient such that the inflatable section of the cuff lies directly over the brachial artery, and then occludes the artery by inflating the inflatable section to a pressure exceeding the systolic pressure of the artery. The health care provider then slowly decreases pressure in the bladder, and with use of a stethoscope, listens for changes in the sound made by blood flowing through the artery.

At the point where the bladder pressure equals the systolic pressure of the artery, blood begins to flow through the artery. The pressure reading of the bladder at the time blood flow becomes audible is the systolic pressure of the artery.

For accurate blood pressure reading, the inflatable section of the cuff must occlude a substantial length of the brachial artery. Most studies conclude that an inflatable section width of about 40 percent of the circumference of an arm will ensure adequate occlusion of the artery. If the bladder occludes only a short length of artery then the pressure reading of the bladder at the time the blood begins to flow through the artery will be greater than the actual systolic pressure of the artery, resulting in an erroneously high systolic blood pressure reading.

A conventional cuff design of the prior art includes a rectangular shaped end portion which is adapted to be wrapped uniformly about substantially cylindrical objects. Because the majority of patients have biceps of substantially uniform circumference, the conventional cuff design of the prior art applies even pressure along a substantial length of the brachial artery during blood pressure reading and is therefore effective in providing accurate blood pressure readings in most cases.

Unfortunately, some patients, particularly overweight patients, do not have arms of substantially uniform circumference. When a blood pressure cuff of a conventional design is applied to patients having nonuniform-circumferenced, or "tapered" arms, the bladder portion of the cuff tends to apply significant pressure only to a short length of the brachial artery, and leads to erroneous blood pressure readings.

Pressure cuffs having essentially the same design as blood pressure cuffs are used for a variety of medical procedures including plethysmography.

There exists a need for a pressure cuff which can accurately and reliably apply substantial even cuff pressure to the arms of patients having arms of substantially nonuniform circumference.

SUMMARY OF THE INVENTION

According to its major aspects and broadly stated the present invention is an improved blood pressure cuff which is adapted to accurately and reliably apply substantially even cuff pressure across a substantial length of a brachial artery to the arms of patients having arms of substantially nonuniform circumference.

In the blood pressure cuff of the present invention, an end portion of a cuff comprises a pair of separable first and second tail sections, each having a coupling mechanism, such as sections of hook and loop type fastening material formed thereon. A complementary coupling mechanism is formed on the inflatable section. When the cuff is wrapped about an arm having a nonuniform circumference, then the tail sections can be coupled at different lengths to the inflatable section of the cuff, so that the inflatable section, when inflated, supplies relatively even pressure across a substantial length of the brachial artery.

In one embodiment of the invention, a coupling mechanism is formed on at least one exterior surface of a tail section. In the case that the second tail section, after being coupled to an inflatable section coupling mechanism, covers a substantial portion of the inflatable section coupling mechanism, the coupling mechanism of an interior surface of a first tail section can be coupled with a coupling mechanism of an exterior surface of a second tail section.

These and other details, advantages and benefits of the present invention will become apparent from the detailed description of the preferred embodiment hereinbelow.

BRIEF DESCRIPTION OF THE DRAWINGS

The preferred embodiment of the invention will now be described, by way of example only, with reference to the accompanying figures wherein like members bear like reference numerals and wherein:

FIG. 2A is an exterior view of a blood pressure cuff according to the invention;

FIG. 2B is an interior view of a blood pressure cuff according to the invention;

DETAILED DESCRIPTION OF THE PREFERRED EMBODIMENTS

For a better understanding of the present invention, it is useful first to consider the problem which the present invention solves.

Figure 1:
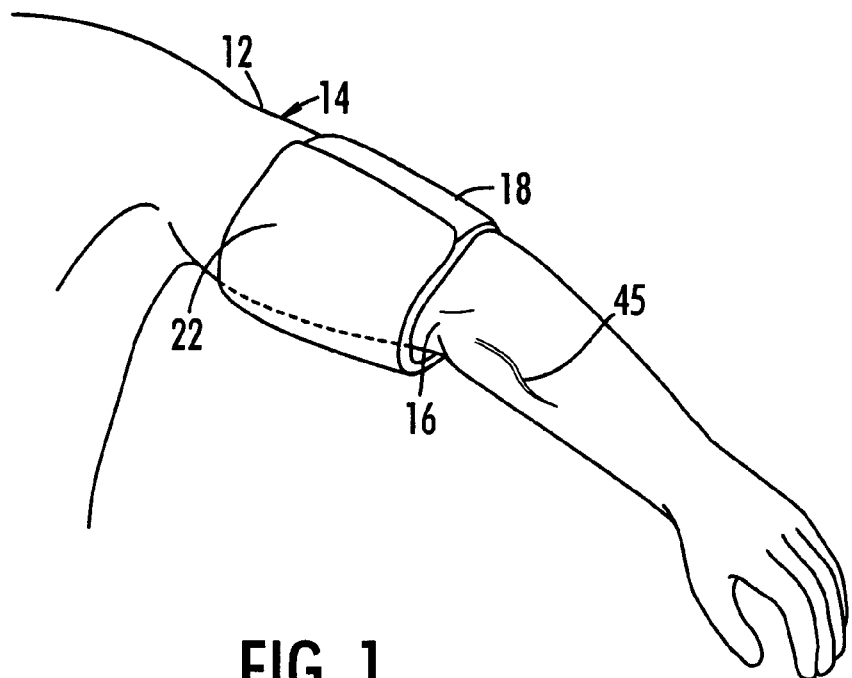
FIG. 1 shows a prior art blood pressure cuff applied to an upper arm member having a substantially nonuniform circumference.
Figure 3:
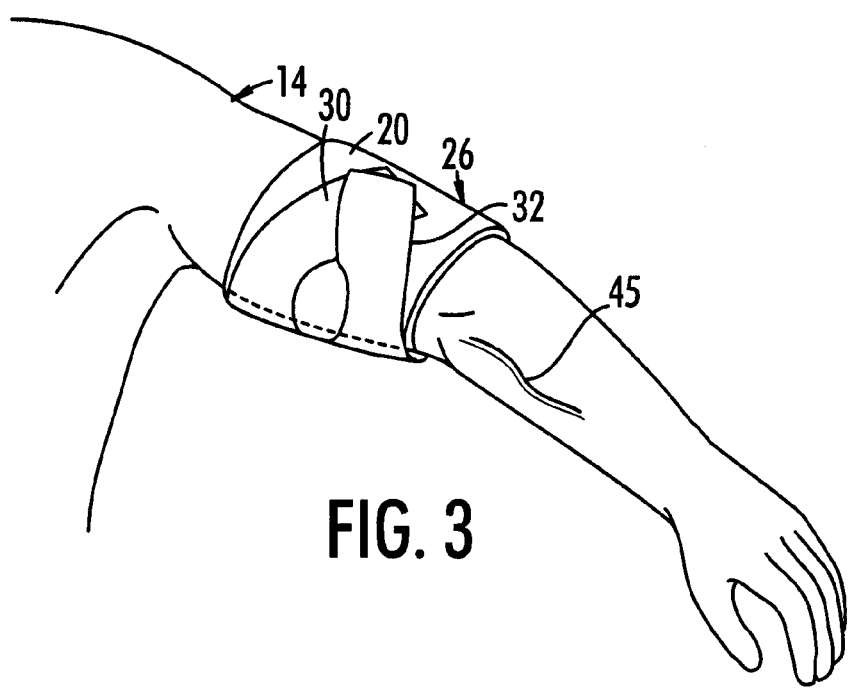
FIG. 3 shows a blood pressure cuff according to the invention applied to an upper arm member having a substantially nonuniform circumference.

FIG. 1 shows a prior art blood pressure cuff applied to a patient having an upper arm member of a substantially non-uniform circumference. The arm member 12 of the patient shown has a larger circumference at the upper end 14 of the arm member then at the lower end 16. This shape of upper arm member, common in overweight patients, may be referred to as a "tapered" arm. Referring to aspects of the prior art blood pressure cuff, blood pressure cuff 18 includes an inflatable section and a substantially rectangular end section 22. It can be seen that if cuff 18 were applied to a patient having an arm of uniform circumference and inflated that cuff 18 would apply relatively even pressure along a substantial length of artery 45. However, where cuff 18 having a rectangular end section is applied to a tapered arm, as in the case shown, cuff 18 tends to apply greater pressure toward upper end 14 of arm 12 than toward lower end 16. As such, cuff 18 tends to occlude only a small length of the brachial artery when inflated after being applied to a tapered or otherwise nonuniform-circumferenced arm.

In one type of blood pressure cuff, inflatable section 20 includes a cavity and a latex inflatable bladder deposited in the cavity. In another common type of cuff known as a "bladderless" cuff, the inflatable section 20 comprises opposing sections of flexible material (typically made of nylon) joined peripherally in a seal tight fashion.

Because cuff 18 occludes only a small length of the brachial artery, the pressure reading of the cuff inflatable section at the time blood begins to flow through artery is greater than the actual systolic pressure of the artery, yielding an erroneous reading of systolic pressure. The pressure reading from cuff 18 is normally erroneously high in the case where cuff 18 occludes only a short length of artery.

A blood pressure cuff 20 according to the invention is described with reference to FIGS. 2A through 4C. Cuff 20 having an interior surface 23 and an exterior surface 24 includes an inflatable section 26 and an end section 28. In one embodiment, end section 28 includes first and second independently moveable tail sections 30 and 32. Coupling mechanisms 34 and 35 are formed on the bottom or interior surface of both tail sections 30 and 32 and a complementary bladder coupling mechanism 36 for coupling with either coupling mechanism 34 or coupling mechanism 35 is formed on exterior surface 24 of inflatable section 26. Coupling mechanisms 34, 35, and 36 are typically provided by sections of hook and loop type fastening material, such as VELCRO. In a preferred embodiment, tail sections 30 and 32 each include additional coupling mechanisms 38 and 39 formed on the top or exterior surfaces 24 thereof. The exterior surface coupling mechanisms of tail sections 30 and 32 should be complementarily formed to couple with the interior surface coupling mechanisms of the tail sections 30 and 32. Exterior surface coupling mechanisms 38 and 39 are also conveniently supplied by strips of hook and loop type fastening material.

Cuff 20 typically comprises a rugged flexible material such as nylon or canvass. Tail sections 30 and 32 may be formed, for example, by forming a slit 40 in a rectangular end section, to thereby form tail sections 30 and 32. In a preferred embodiment, end section 28 of cuff 20 comprises specially configured slit 40 which included at its interior end a cutaway region 42. Cutaway region 42 prevents buckling or "puckering" of extraneous cuff material when tail sections 30 and 32 are moved crosswise with respect to one another.

FIGS. 3, 4A, 4B and 4C illustrates the cuff shown in FIGS. 2A and 2B in use being wrapped around an upper arm member of substantially nonuniform circumference. It is seen that when cuff 20 is wrapped around an upper arm member 14, second tail section 32 positioned toward narrow region of arm 14 can be extended across inflatable section 20 for coupling with inflatable section coupling mechanism a greater distance then first tail section (position toward a wider region of arm) so that inflatable section 26, when inflated, imparts a substantially uniform force throughout a substantial length of the brachial artery 45.

Figure 4A:
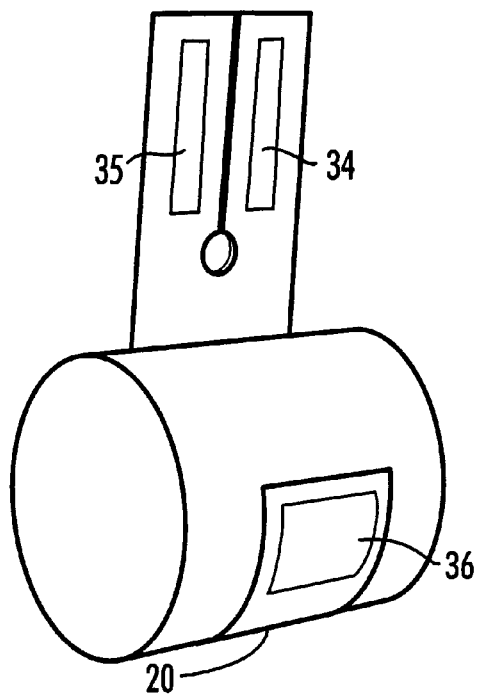
FIGS. 4A, 4B and 4C show a blood pressure cuff according to the invention illustrating stages of application of the cuff to a patient's arm.
Figure 4B:
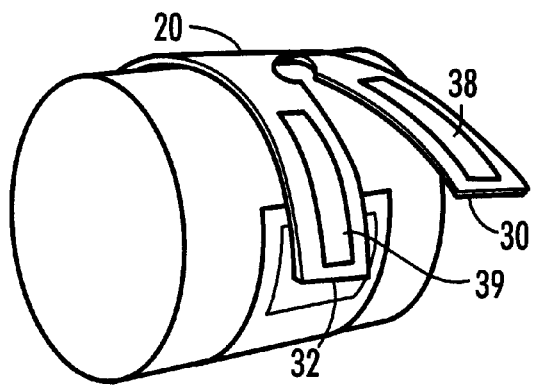
Figure 4C:
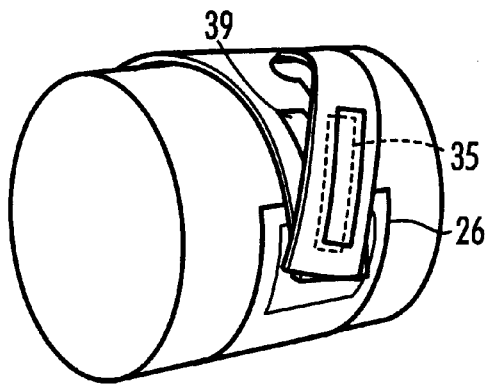

During application of cuff 20 to a tapered arm, first tail section 30 will be extended crosswise with respect to second tail section 32 as best seen in FIG. 4C in order to snugly and uniformly fit cuff 26 on arm 14. In the case illustrated, interior coupling mechanism 35 of first tail section 30 is conveniently coupled with exterior coupling mechanism 39 of second tail 32. Interior coupling mechanism 35 may also conveniently be partially coupled with coupling mechanism 39 and inflatable section coupling mechanism 36. It is especially useful to couple first tail interior section coupling mechanism 35 at least partially with second tail exterior coupling mechanism 39 considering that tail 32, after being coupled with inflatable section 26 may cover a substantial area of the coupling mechanism of inflatable section 26.

Figure 5A:
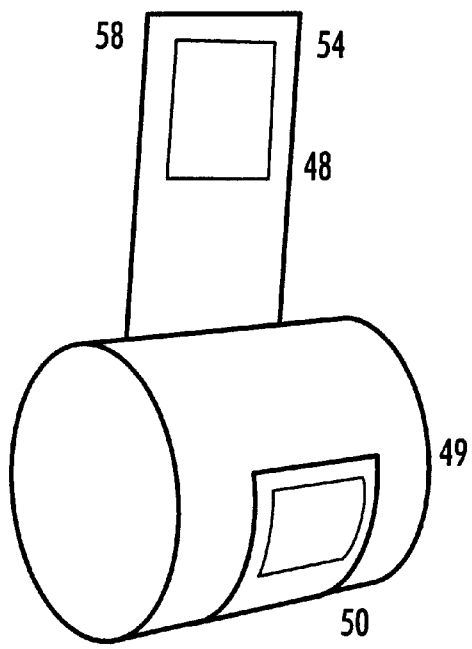
FIGS. 5A, 5B and 5C show an alternative embodiment of a cuff according to the invention illustrating stages of application of the cuff to a patient's arm.
Figure 5B:
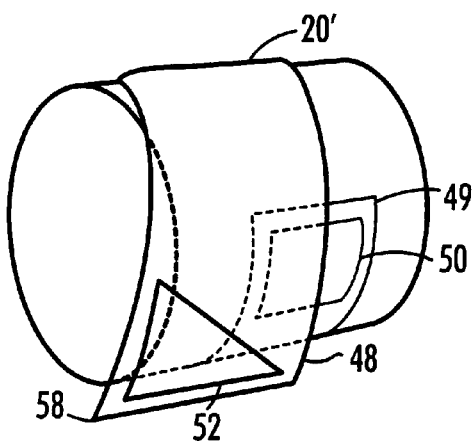
Figure 5C:
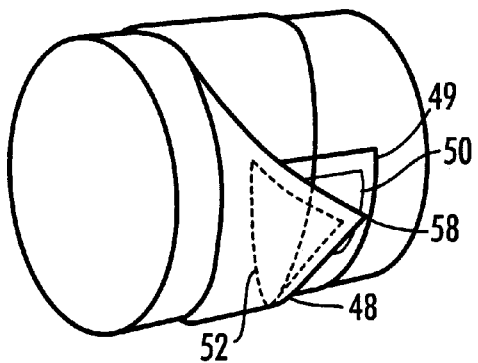

An alternative embodiment of the invention is described with reference to FIGS. 5A, 5B and 5C. In this embodiment, a generally rectangular cuff end section 48 is provided and a coupling mechanism 52 adapted for coupling with interior surface coupling mechanism 50 which is formed on the exterior surface of inflatable section 49 as is illustrated in FIGS. 5A–5C.

Forming coupling mechanism 52 on the exterior surface of end section 48 enables cuff 20' to be applied to nonuniform circumference arm members such that substantial lengths of brachial arteries are occluded on such arms. It is seen that first corner 54 of end section 48 may be extended over inflatable bladder section 49 and coupled to coupling mechanism 50, while second corner 58 of end section 48 may be folded over a portion of end section 48 and coupled with an exposed portion of coupling mechanism 50 on the exterior surface of an inflatable section 49.

While this invention has been described in detail with reference to a preferred embodiment, it should be appreciated that the present invention is not limited to that precise embodiment. Rather, in view of the present disclosure which describes the best mode for practicing the invention, many modifications and variations would present themselves to those skilled in the art without departing from the scope and spirit of this invention, as defined in the following claims.

What is claimed is:

1. A pressure cuff for use in reading pressure, said cuff comprising:

an inflatable section;

an end section extending from said inflatable section, said end section comprising first and second tail sections;

an inflatable section coupling mechanism formed on an exterior surface of said inflatable section;

first and second interior coupling mechanisms formed, respectively, on interior surfaces of each of said first and second tail sections.

2. The pressure cuff of claim 1, further comprising:

at least one exterior coupling mechanism formed on either of said first or second tail sections.

3. The pressure cuff of claim 1, wherein said end section comprises a slit defining said first and second tail sections.

4. The pressure cuff of claim 1, wherein said end section comprises a slit terminating in a widened region defining said first and second tail sections.

5. The pressure cuff of claim 1, wherein said inflatable section comprises an inflatable bladder.

6. A pressure cuff for use in reading blood pressure, said cuff comprising:

an inflatable section;

an end section extending from said inflatable section;

an inflatable section coupling mechanism formed on an exterior surface of said inflatable section;

an end section coupling mechanism formed on an exterior surface of said end section.

7. The pressure cuff of claim 6, wherein said inflatable section comprises an inflatable bladder.

\* \* \* \* \*